United States Patent [19]
Jaeger

[11] 4,147,062
[45] Apr. 3, 1979

[54] LIQUID SAMPLER
[76] Inventor: Ben E. Jaeger, Rte. 2, Box 49, Plano, Ill. 60545
[21] Appl. No.: 882,775
[22] Filed: Mar. 2, 1978
[51] Int. Cl.$^2$ .............................................. G01N 1/14
[52] U.S. Cl. ................................................ 73/422 GC
[58] Field of Search ....... 73/421 B, 422 GC, 422 TC, 73/423

[56] References Cited
U.S. PATENT DOCUMENTS
2,598,535  5/1952  Green .............................. 73/422 TC FOREIGN PATENT DOCUMENTS
2648330  1/1978  Fed. Rep. of Germany ......... 73/421 B Primary Examiner—S. Clement Swisher
Attorney, Agent, or Firm—Gary, Juettner & Pyle

[57] ABSTRACT

A sampling apparatus is characterized by a housing having a bore extending therethrough, which is supported with one end of the bore communicating with the interior of a liquid containing vessel and with an opposite end of the bore being outside of the vessel. A plunger or cylinder rod is positioned in the bore and has an annular recess intermediate its ends of a length longitudinally of the plunger which is less than the length of the bore. A pneumatic cylinder is connected with the plunger at the opposite end of the bore for reciprocating the plunger in the bore to project the recess into the vessel to receive a sample of liqud therein, and to then move the recess from the vessel and to an intermediate point in the bore whereat a housing outlet port receives the sample. First and second seals on the plunger to opposite sides of the recess maintain a liquid seal between the one end of the bore and the outlet port during reciprocation of the plunger, and a third seal is on the plunger toward the opposite end of the bore. The third seal absolutely blocks passage of any sampled liquid to the pneumatic cylinder, and wipes the bore clean between the opposite end thereof and the outlet port with each reciprocation of the plunger.

13 Claims, 8 Drawing Figures

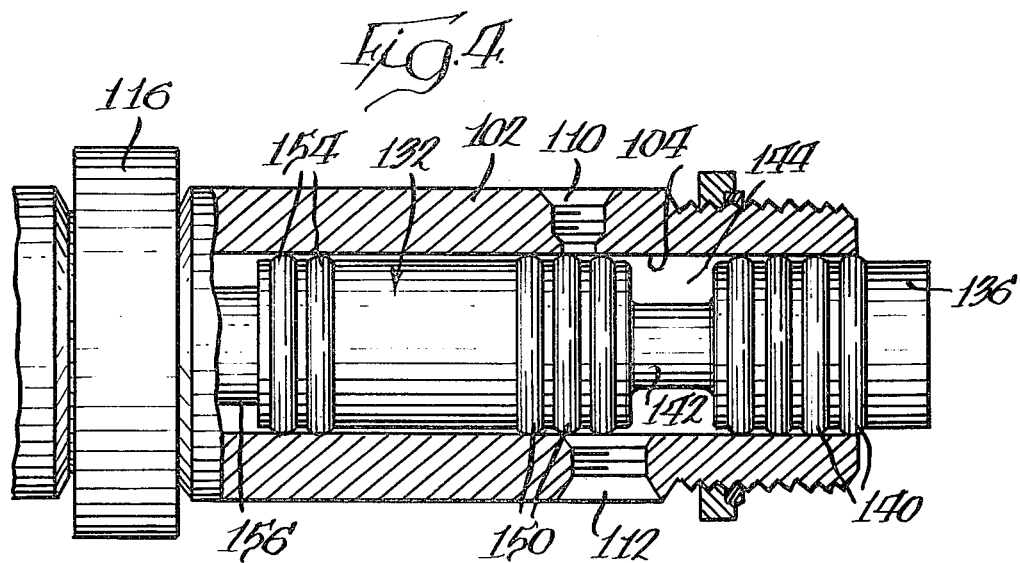
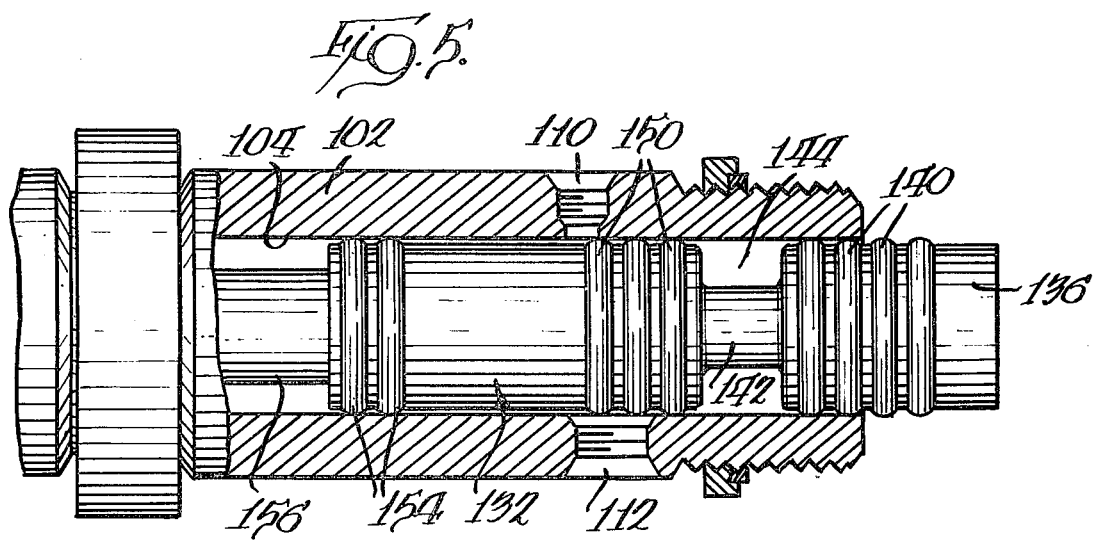
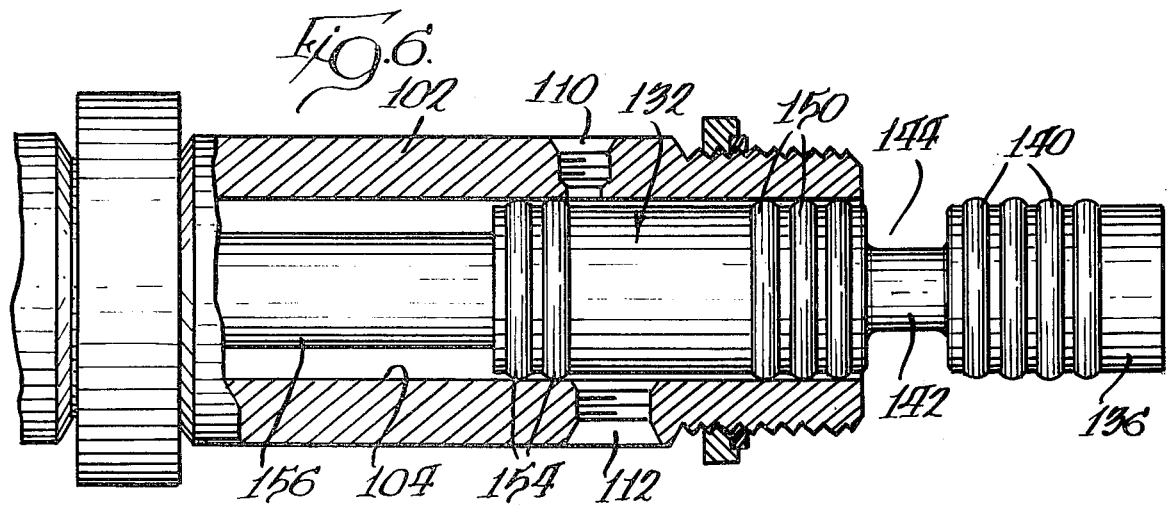

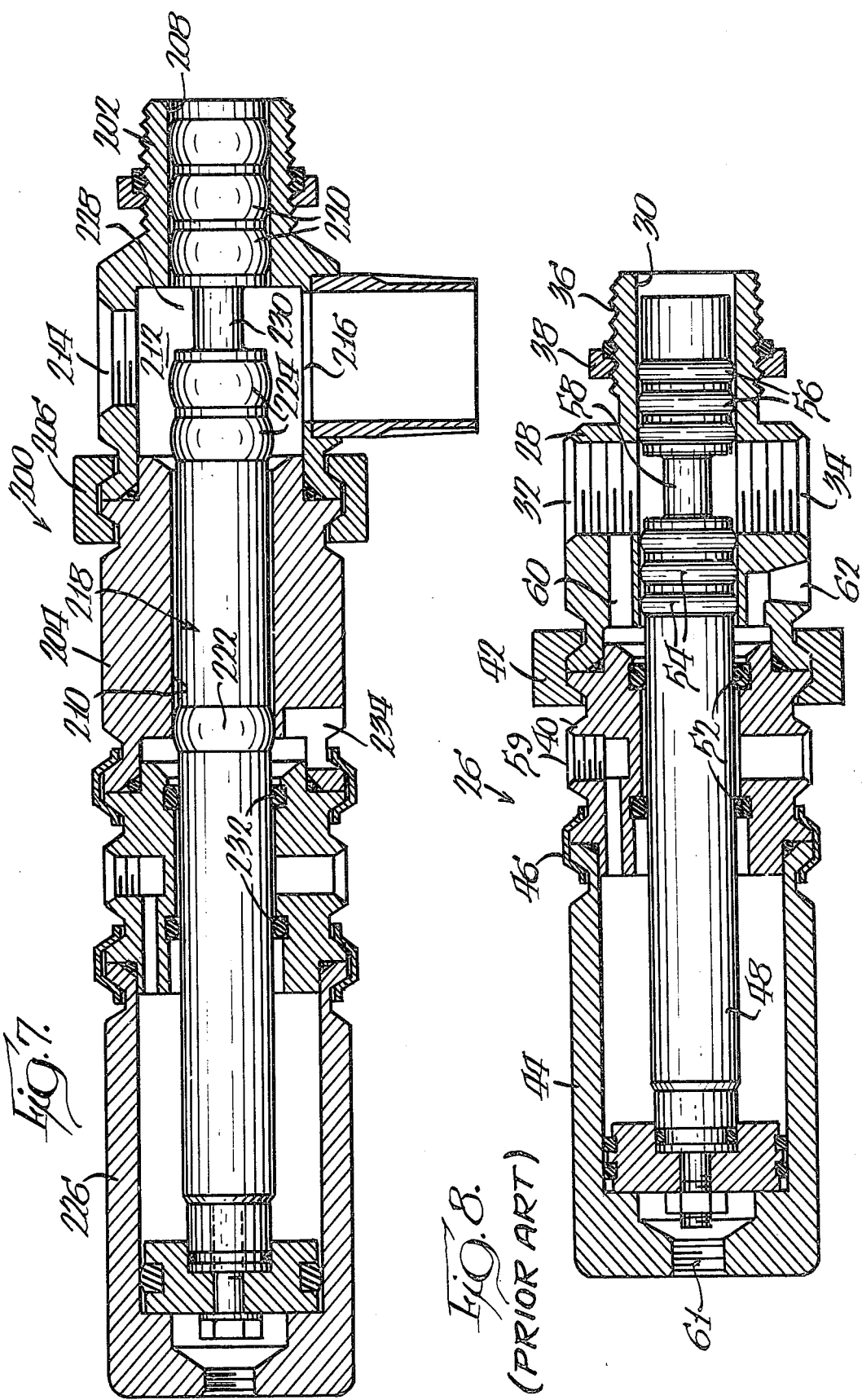

LIQUID SAMPLER

BACKGROUND OF THE INVENTION

The present invention relates to apparatus for extracting samples of liquid from flow lines or tanks thereof.

Various manufacturing operations require that the immediate or overall composition of a liquid flowing through a pipe or conduit be monitored or determined. Such monitoring ordinarily is accomplished with apparatus, sometimes denoted as samplers, which take samples of liquid from the main body thereof. Where a composite sample of the liquid flow is required, the sampler is usually operated to withdraw a series of small, measured amounts of the liquid as it passes a sampling point. The individual samples are collected, and represent a composite sample of the total volume of liquid.

One instance in which composite sampling is used, for example, is in determining the fat content of milk. Milk received by a dairy from individual dairy farmers is pumped into a large storage tank. Since the batches of milk supplied by the individual dairy farmers ordinarily differ in fat content, stratified layers of milk of various fat content are formed in the tank. To determine the overall fat content of the milk in the tank, the milk could be thoroughly stirred and then sampled, but this is expensive and time consuming. Instead, as the milk is removed from the tank through a conduit it is advantageous to periodically extract and collect discrete and measured amounts of milk from the conduit to obtain a composite sample of the milk in the tank. The sample may then be analyzed for fat content, which represents the overall fat content of the milk.

Other uses for samplers are in on-line analysis applications in which the immediate composition of a liquid must be determined. For this application, the individual samples of liquid are not collected as a composite sample, but instead are separately analyzed.

To obtain the samples, some samplers continuously divert streams of liquid from the flow lines or tanks, and from the diverted streams the samples are removed in various ways. Attempts to withdraw small measured quantities directly from the pipes or tanks, however, have presented many problems not satisfactorily solved. For example, liquid receiving holes or slots in samplers adapted to be extended directly into a pipe require an orienting mechanism, and the sampled material often builds up in such holes and slots and either blocks the same or contaminates subsequent samples. Such samplers obviously cannot be used where a high degree of sanitation is required, such as in the sampling of food products, and are ill suited to handle high viscosity or thixotropic liquids. In addition, conventional samplers are difficult to disassemble for inspection, cleaning and replacement of parts, and excessive leakage and clogging of the samplers are problems common to many types of samplers.

OBJECTS OF THE INVENTION

An object of the present invention is to provide a sampler which can withdraw small measured quantities of samples directly from either a pipe or a tank, unaccompanied by excessive leakage.

Another object of the invention is to provide a sampler which cannot become clogged by the material to be sampled.

A further object of the invention is to provide a sampler which is excellently suited for automatic operation at selected intervals under the control of a timing mechanism.

Yet another object of the invention is to provide a sampler which is self-cleaning in its operation, and which may readily be flushed with a solvent or autoclaved.

A still further object of the invention is to provide a sampler which is of simple and economical construction, and which may easily be disassembled for inspection, cleaning and replacement of parts.

Yet still another object of the invention is to provide a sampler which is pneumatically or electrically operated and formed as a single unit with the operating means, and which includes improved seal means for preventing sampled material from entering the operating means.

SUMMARY OF THE INVENTION

In accordance with the present invention, an apparatus for obtaining discrete and measured samples of a liquid from a vessel comprises a housing having a cylindrical bore extending therethrough. The housing is supported with one end of the bore communicating with the interior of the vessel and with the opposite end of the bore extending to outside of the vessel, and a cylindrical plunger is positioned in the bore for reciprocation therein. An annular recess is formed in the surface of the plunger intermediate its ends, and is of a length along the axis of the rod which is less than the length of the bore. A port in the housing communicates with the bore between opposite ends thereof, and means are provided at the opposite end of the bore for reciprocating the plunger to project the recess into the interior of the vessel to receive a sample of liquid therein, and to then withdraw the recess from the vessel and to the port in the bore for discharge of the sample through the port. First and second seals are provided on the plunger to opposite sides of the recess to maintain a liquid seal between the one end of the bore and the port during reciprocation of the plunger, and a third seal is on the plunger toward the opposite end of the bore. The third seal maintains a liquid seal between the opposite end of the bore and the port to absolutely prevent passage of any sampled material to the means for reciprocating, and wipes that portion of the bore clean of any liquid with each reciprocation of the rod in the bore.

The foregoing and other objects, advantages and features of the invention will become apparent upon a consideration of the following detailed description, when taken in conjunction with the accompanying drawings.

BRIEF DESCRIPTION OF THE DRAWINGS

FIGS. 4-6 are views of the sample obtaining portion of the structure shown in FIG. 3, and illustrate sequential stages of operation of the sampler in obtaining a sample of liquid from the conduit;

FIG. 7 is a cross-sectional elevation view of a sampler in accordance with another embodiment of the invention, and also illustrates a pneumatic cylinder for operating the sampler, and FIG. 8 is a cross-sectional elevation view of a prior art sampler.

DETAILED DESCRIPTION

Figure 2:
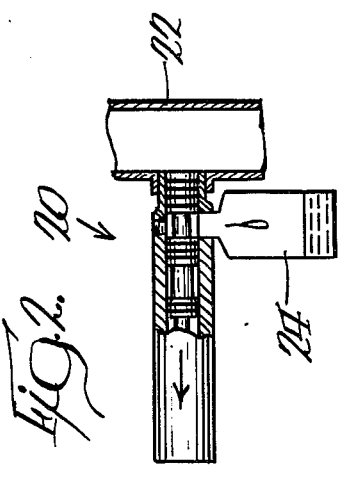
FIG. 2 is similar to FIG. 1, and shows the plunger of the sampler withdrawn from the conduit to a position whereat the sample is discharged into a container.
Figure 1:
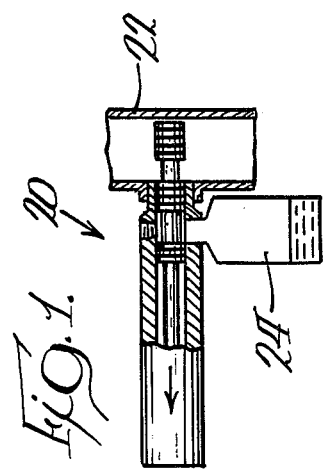
FIG. 1 is a schematic representation of a liquid sampler embodying the teachings of the present invention, showing a plunger of the sampler extended into a conduit for obtaining a measured sample of a liquid flowing therein.

Referring to FIGS. 1 and 2 there is shown a schematic representation of a sampler, indicated generally at 20, in accordance with one embodiment of the invention. The sampler includes a plunger having an annular recess which is extendable into a conduit 22 for receiving a sample of a liquid flowing therein, and which is then retractable to exterior of the conduit for collection of the sample in a container 24. The recess is of a size to contain a precisely measured amount of the liquid, and the sampler may be cyclically actuated so that the material in the container represents a composite sample of the liquid flowing through the conduit. The plunger may be actuated by a pneumatic or electric motor mounted on a rearward end of the sampler, and a plurality of seals in the plunger maintain a liquid seal between the interior of the conduit and the container, and between the container and the motor, during reciprocation of the plunger. In this manner, the sampler is generally insensitive to the pressure of the liquid in the conduit, and the collected sample is protected against contamination.

As may be appreciated, the annular recess which forms the sample chamber is washed clean by the liquid each time it is extended into the conduit, movement of the sample of liquid to the container is accomplished smoothly and without any slots or passages to clog, and there are no lines, diaphragms or pumps to impose internal shear or churning of the sample, whereby the samples collected in the container are true samples of the liquid in the conduit.

THE PRIOR ART

In order to better appreciate the advantages and features of the present invention, reference is first made to FIG. 8 in which is shown a sampler, indicated generally at 26, which is superficially similar to the samplers of the invention, but is of a conventional type. The sampler includes a forward body 28 having a bore 30 and inlet and outlet ports 32 and 34, respectively, in communication with the bore. Threads 36 on a forward end of the body enable the body to be mounted in an opening in a liquid carrying conduct, with a lock nut 38 securing the body with the conduit.

The rearward end of the body is connected with one end of a head 40 by means of a clamp 42, and the opposite end of the head is connected with a cylinder barrel 44 by means of a clamp 46. The head has a bore 45 therein which is aligned with the bore 30, and a cylinder rod 48 is extended through the bores for reciprocation therein by a piston 50 in the barrel.

A pair of seals 52 in the head 40 maintains a fluid seal in the bore 45, and first and second sets of seals 54 and 56 on the cylinder rod provide a liquid seal between the rod and the bore 30. An annular recess 58 is formed in the rod between the seals 54 and 56, and air inlet means 59 and 61 are provided for selectively introducing air into the barrel 44 to one side or the other of the piston to reciprocate the rod within the bores. Upon the rod being reciprocated to the right (as shown in the drawing), the recess is moved out of the bore 30 and extended into the conduit for receiving a sample of liquid therein. Then, upon reciprocation of the rod to the left, the recess is moved back into the bore and carries the sample to the outlet port 34 to be discharged therethrough. To this end, to facilitate removal of the sample from the recess, a fluid may be applied through the inlet port 32 to flush the sample therefrom.

The arrangement of the seals 54 and 56 is such that a liquid seal is always maintained between the forward end of the bore 30, and therefore the interior of the conduit, and the inlet and outlet ports. In particular, prior to the leftmost seal 56 exiting the bore, upon rightward movement of the cylinder rod, at least one of the seals 54 is moved beyond the inlet and outlet ports. Consequently, only the sampled portions of the liquid may reach the outlet port.

A problem that arises in the use of such a conventional sampler is that when the cylinder rod is retracted, upon the recess opening to the inlet and outlet ports the liquid therein splashes across the seals 54, which particularly is the case when the liquid is under pressure. In consequence, liquid slowly accumulates in the bore behind the seals 54. The head seals 52 are exposed to this liquid, and where the liquid is abrasive the seals are rapidly worn. The result is that the pneumatic fluid for operating the cylinder is able to pass by the seals to the outlet port, whereby the samples in the container become contaminated, and the liquid is able to enter the air supply system for the pneumatic cylinder. In the case where the liquid is very hazardous, such as where it is radioactive, escape of the liquid into the air supply system is intolerable.

In addition to wear of the head seals 52, liquid accumulating behind the seals 54 may ultimately form a barrier and prevent the cylinder rod from retracting completely. Should this occur, the recess will not be moved fully over the outlet port, and with an additional accumulation of liquid the recess may completely fail to open to the port. This would, of course, render the sampler inoperative.

Prior attempts to overcome these disadvantages contemplate providing either or both of a bypass port 60 between the inlet port 32 and the bore 30 behind the seals 54, and a drain port 62 communicating with the bore behind the seals. It was thought that as liquid accumulated in the bore behind the seals, when the cylinder rod was retracted into the bore the seals would force the liquid through either or both of the ports, thereby preventing an accumulation of the liquid. For certain materials that do not set or harden, the bypass and drain ports did help prevent an accumulation of material, but they did little to protect the seals 52 against the liquid, and the problem of liquid sample and pneumatic fluid contamination persisted. Also, in the case where thixotropic or thermosetting materials were sampled, the bypass and drain ports proved to be quite useless, since upon movement of such materials into the ports the materials hardened and sealed the ports.

THE INVENTION

In accordance with the present invention, there is provided an improved liquid sampler which is uniquely constructed in a manner which overcomes the aforementioned disadvantages of conventional samplers. The sampler has components which may readily be assembled and disassembled for inspection, cleaning or replacement of parts. In addition, the sampler has novel seal means which absolutely prevents passage of pneumatic fluid to the sampled liquid or of the sampled liquid to the pneumatic fluid, which protects the head seals against contact with the sampled liquid, and which cleans the entire plunger bore each time that the plunger is cycled.

Figure 3:
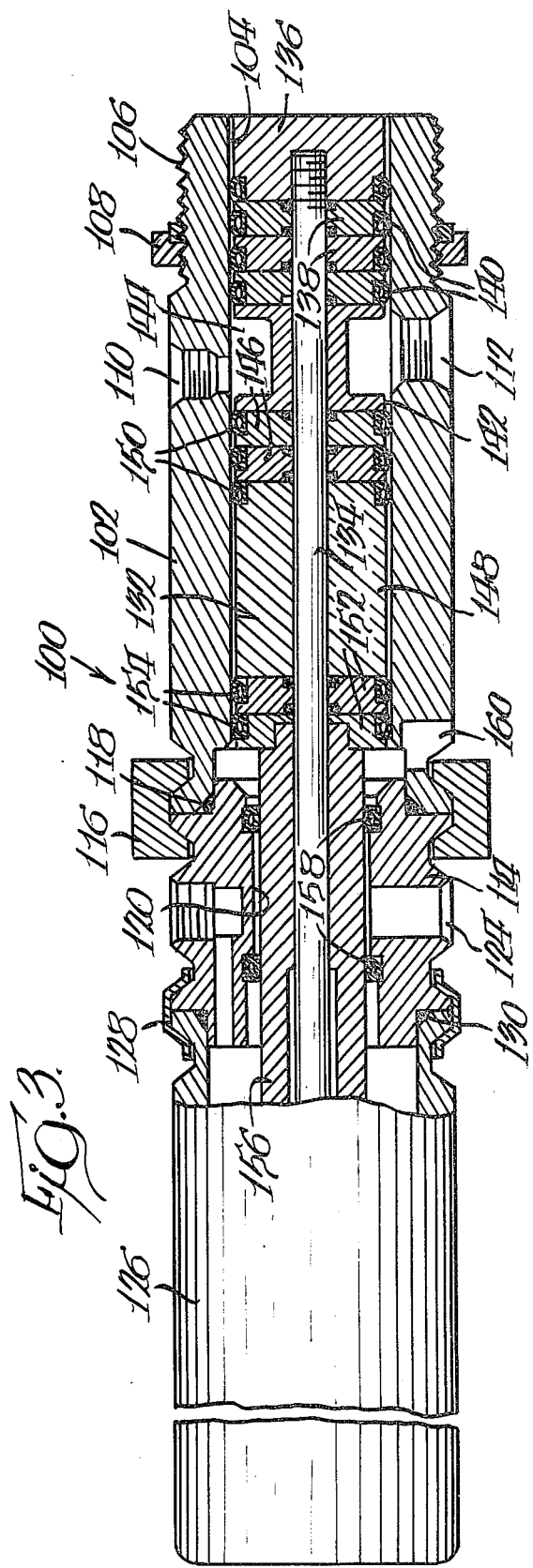
FIG. 3 is a side elevation view, partly in cross section, illustrating a liquid sampler in accordance with one embodiment of the invention.

More specifically, as shown in FIG. 3 and indicated generally at 100, an improved sampler constructed in accordance with one embodiment of the invention includes a body 102 which may be formed of any suitable material, such as plastic or metal, having a bore 104 extending longitudinally therethrough. A forward end of the body has threads 106 for attaching the body within a threaded opening in a wall of a liquid carrying conduit, a lock nut 108 being provided to secure the body to the conduit. Opposed inlet and outlet ports 110 and 112, respectively, are formed through the body and intercept the bore at an intermediate point therealong.

A head 114 is attached to the rearward end of the body 102 by a quick release clamp 116 and is sealed therewith by a head seal 118. The head may be made of plastic, metal or other suitable material, but is preferably of the same material as the body in order that it will have the same coefficient of thermal expansion as the body, thus preventing dimensional operating variations in response to extremes of temperatures. A bore 120 is formed through the head in axial alignment with the bore 104, and a port 124 extends into the head and intersects the bore about medially thereof to provide a drain therefor. A motor which may comprise a pneumatic cylinder 126 is connected to a rearward end of the head by means of a quick release clamp 128, and is sealed therewith by a head seal 130. The pneumatic cylinder may be of the same type as that described with reference to the prior art sampler shown in FIG. 8, and therefore will not be further discussed.

Extending through the bores 104 and 120 is a cylinder rod or plunger assembly, indicated generally at 132, which is constructed in a manner facilitating disassembly thereof for cleaning or replacement of parts. More specifically, the plunger includes an elongated spindle 134 extending along the axis of the plunger and having a cap 136 threaded onto its forward end. Three seal carriers 138 are positioned around the spindle and sealed therewith rearward of the cap, and with the cap support four annular or O-ring seals 140. A spool 142 which defines an annular recess or sample chamber 144 of predetermined volumetric displacement is extended around the spindle rearward of the seal carriers, and a pair of seal carriers 146 are around and sealed with the spindle behind the spool. A spacer 148 is mounted to the rear of the seal carriers 146, and with the seal carriers supports three seals 150. A pair of seal carriers 152 to the rear of the spacer support a pair of seals 154, and a piston rod 156 extends between the seal carriers and a piston in the pneumatic cylinder 126. Actuation of the pneumatic cylinder thus reciprocates the plunger assembly within the bores, with a pair of seals 158 sealing the piston rod with the bore 120.

The cap 136, and spool 142, the spacer 148, the piston rod 156 and the seal carriers 138, 146 and 152 are all of a smaller diameter than the diameter of their respective bores in order to provide a slight clearance therein. In consequence, the annular seals themselves control the concentricity of the plunger assembly within the bores, and function as bearings to enable the plunger assembly to reciprocate easily. This prevents direct sliding contact between the relatively "hard" components of the sampler, whereby the life of the sampler is extended and the repair frequency reduced.

In addition, by virtue of its particular construction, when the need arises to clean, repair or replace components of the sampler, it may readily be disassembled. For example, should any of the particular components of the plunger assembly 132, which are normally positioned within the bore 104, require servicing, the quick release clamp 116 may be removed to enable the forward portion of the plunger assembly to be withdrawn from the bore. Should the piston rod 156 or the seals 158 require service, upon removal of the plunger assembly from the bore 104 as above discussed, the cap 136 may be unthreaded from the spindle 134 to enable the forward components of the plunger assembly to be moved off of the spindle. The quick release clamp 128 may then be removed to allow separation of the head 114 from the pneumatic cylinder 126 to expose the piston rod and the seals. The sampler may thus be quickly and economically serviced without being taken out of use for an extended period of time.

Referring also to FIGS. 4-6 which illustrate various positions of the plunger assembly within the bore 104 as it is reciprocated to extract a sample of liquid from the conduit, it may be seen that the particular arrangement of the seals 140 and 150 at all times maintains a liquid seal between the inlet and outlet ports 110 and 112 and the liquid in the conduit. In addition, the seals 140, 150 and 154 wipe the bore clean of sampled liquid with each reciprocation of the plunger assembly, and prevent any of the liquid from moving to behind the seals 154, whereat the liquid would adversely affect the seals 158 and ultimately form a barrier to prevent complete retraction of the plunger assembly.

In particular, upon movement of the plunger assembly 132 out of the bore 104 to position the spool 142 with its sample chamber 144 within the conduit, the seals 154 move from the rearward end of the bore to adjacent the ports 110 and 112 to squeegee and wipe the bore clean of any liquid that may have accumulated behind the seals 150, and the seals 150 move from the ports to adjacent the forward end of the bore to wipe clean that portion of the bore. In this manner, the bore is cleaned of any accumulated liquid with each reciprocation of the plunger assembly.

It is also to be noted that as the plunger assembly moves out of the bore, the seals 150 form a liquid seal with the bore forward of the inlet and the outlet ports before all of the seals 140 move out of the bore. Similarly, upon retraction of the plunger into the bore, at least some of the seals 140 enter the bore before the seals 150 expose the ports. In consequence, a liquid seal is at all times maintained between the liquid under pressure in the conduit and the inlet and outlet ports, and only the liquid sample in the recess ever reaches the ports.

Upon extending the plunger assembly to obtain a sample, it is to be appreciated that the spool 142 is projected into the conduit and exposed to the stream of liquid. Thus, the annular recess is washed by the product stream upon each cycle of operation of the sampler. This minimizes a buildup of product in the sample chamber, as is typical in conventional samplers which use slots or holes for collecting a sample, since the particular shape of the recess and its direct exposure to the stream of product prevent it from becoming clogged by solids, and the collecting chamber is therefore self cleaning of debris often encountered in product or drain lines, such as rags, filaments from filter cloths, tough and stringy chunks of product, wood chips, etc. It is therefore apparent that when the recess is withdrawn into the bore, it will carry a true sample of the liquid.

Upon the plunger being fully retracted into the bore, it will occupy the position shown in FIG. 3. At this point, the annular recess or sample chamber 144 is positioned over the outlet port 112, so that the liquid sample in the recess may pass through the port for immediate analysis or collection in a suitable container (not shown). To facilitate removal of the sample from the recess in the case of high viscosity or thixotropic materials, a stream of air or other suitable fluid can be applied through the inlet portion 110 to flush the sample from the recess, or a vacuum may be applied to the outlet port. This enables substantially any type of liquid to readily be ejected from the sample chamber.

As previously discussed, the novel construction of the sampler facilitates disassembly of the same for cleaning. It is not necessary, however, to disassemble the sampler in order to clean the majority of its components. To this end, the sampler may be cleaned while in its assembled state by injecting a suitable fluid, such as water or a solvent, through the inlet port 110 while reciprocating the plunger. This will cause the injected fluid to flow over and clean all of the working components of the sampler, and to then exit through the outlet port 112. If desired, and particularly where the sample must be sterilized for operation with food products, the sampler may be autoclaved by the simple expedient of injecting steam into the inlet port while reciprocating the plunger assembly.

It is to be noted that unlike the prior art sampler illustrated in FIG. 8, in the sampler of the invention there is no bypass port between the inlet port 110 and the space between the body 102 and the head 114, since the seals 154 absolutely prevent passage of any material therebehind. There is, however, an opening 160 communicating with the space, which is similar to the drain port in the conventional sampler, but which is provided for an entirely different purpose. The opening does not function as a drain for liquid, since none accumulates in the space. Instead, the opening vents the space to atmosphere, so that upon outward reciprocation of the plunger assembly a vacuum is not created behind the seals 154, which might otherwise have the effect of forcefully drawing liquid past the seals and/or drawing pneumatic fluid past the seals 158, and so that upon inward reciprocation of the plunger a positive pressure is not created behind the seals 154 to retard movement of the plunger.

FIG. 7 illustrates another embodiment of a sampler, indicated generally at 200, constructed in accordance with the teachings of the present invention. The primary difference between this sampler and the one previously discussed is that the forward end of the sampler is comprised of two body portions 202 and 204 joined together by a clamp 206 and having respective axially aligned bores 208 and 210. The body portions form an enlarged sample receiving chamber 212 which intersects the bores, and an inlet port 214 and an outlet port 216 are formed through the body portion 202 in communication with the chamber. A plunger assembly, indicated generally at 218, is extended through the bores, and differs from the previously discussed plunger assembly in that only three seals 220 are at a forward end thereof, only one seal 222 is at a rearward end thereof, and only two seals 224 are around a center area thereof and normally received in the chamber 212.

The operation of the sampler 200 is similar to that of the sampler 100, with the plunger first being extendable by a pneumatic cylinder 226 to collect a sample of a liquid in a recess 228 of a spool 230, and then being retractable to move the sample into the sample receiving chamber 212 from which the sample passes through the outlet port 216. During reciprocation of the plunger the seals 220 and 224 always maintain a fluid seal between the sample receiving chamber and the liquid in the conduit, and the seals 222 and 224 wipe the bores 210 and 208 clean of liquid. In consequence, the sampled liquid never enters behind the seal 222 to retard rearward movement of the plunger assembly or to cause adverse wear to a pair of piston rod seals 232. Accordingly, there is no need to provide liquid drain means for the area behind the seal 222, an opening 234 to atmosphere being provided solely for the purpose of preventing a negative or a positive pressure from developing in the area.

The primary advantage of the sampler 200 is that the enlarged sample receiving chamber 212 facilitates sampling of highly viscous or abrasive slurries. To this end, upon fluid being introduced through the inlet port 214 to flush a sample from the annular recess 228, the enlarged chamber causes an increased agitation of the fluid to enhance its action in flushing the sample out of the recess. During such flushing, since the seals 224 are positioned within the chamber, the seals themselves are cleaned, which in the case of an abrasive slurry sample decreases the wear experienced by the seals as they are reciprocated through the bore 208.

The invention thus provides improved embodiments of liquid samplers. By virtue of the particular shape of the annular sample collecting chamber, the chamber is washed clean by the product stream with each cycle of operation, and a stream of gas, air or other suitable fluid can be used to readily eject high viscosity and thixotropic samples from the sample chamber. In addition, the rearmost seals on the plunger assembly, along with the center seals, provide for thorough cleaning of the plunger bore with each cycle of operation of the sampler, with the rearmost seals additionally preventing entry behind the plunger of any portion of the samples. This advantageously prevents an accumulation of liquid behind the plunger which can act as a barrier to prevent complete retraction of the plunger, and protects the piston rod seals against contact with the liquid and destruction. In this manner, not only is the pneumatic fluid for operating the air cylinder prevented from contaminating the samples of liquid, but also the liquid is prevented from escaping from the sampler, as for example through the air supply system for the cylinder, which is extremely important in the case where the liquid is very hazardous, as for example where the liquid is radioactive.

The samplers may readily be constructed of any suitable material, such as corosion resistant metals or plastic, and because the plunger assembly seals themselves function as bearings for the plunger, wear of components is minimized. By the use of releasable clamps to hold together the major body portions of the samplers, the same may be quickly disassembled for inspection, cleaning or replacement of parts, particularly for the replacement of the seals, which tend to wear more rapidly than other portions of the samplers. The inlet and outlet ports enable the application of a fluid or a vacuum to the sample in the recess for quickly removing the same, and flushing mediums can be introduced through the ports to clean accumulated materials from the samplers without disassembly.

It is also to be appreciated that as a result of the particular shape of the sample collecting chamber and the mode of operation of the samplers, the samplers can remove positive displacement samples from a product system without imposing internal shear on the sample, such as is effected by conventional pumping devices, whereby the samples are a true representation of the product. Further, the samplers are excellently suited for automatic operation at selected intervals, for example under the control of a timing mechanism, and since the sample chamber extracts a predetermined and fixed volume of product with each cycle of operation of the sampler, when the samples are collected a composite sample is generated that fully represents the process material composition.

It is also within the contemplation of the invention that samples could be collected from stratified layers of product in a tank. In this case, the sampler is connected to a probe and extended into the tank to a selected layer of product, and is then cycled. It is understood, of course. that in this use of the sampler the inlet and outlet ports communicating with the sample chamber would be closed during sampling.

While embodiments of the invention have been described in detail, various modifications and other embodiments thereof may be devised by one skilled in the art without departing from the spirit and the scope of the invention, as defined by the appended claims.

What is claimed is:

1. A sampling apparatus, comprising a housing having a bore extending therethrough, means for supporting said housing with one end of said bore communicating with the interior of a product containing vessel and with an opposite end of said bore being outside of the vessel; a plunger in the bore and reciprocable therein, said plunger having a recess therein intermediate its ends and of a length longitudinally of said plunger less than the length of said bore; means at said opposite end of said bore connected with said plunger for reciprocating said plunger in said bore to project said recess into said vessel to receive a sample of product therein and to then retract said recess from said vessel to a point in said bore outside of said vessel and intermediate the ends thereof; means at said point in said bore for receiving the sample of product in said recess; means for maintaining a liquid seal between said one end of said bore and said point therein; and seal means on said plunger toward said opposite end of said bore for maintaining a liquid seal between said point in said bore and said opposite end thereof, and therefore between said point and said means for reciprocating.

2. A sampling apparatus as set forth in claim 1, said means for maintaining a liquid seal between said one end of said bore and said point therein comprising first and second seal means on said plunger on opposite sides of said recess, said seal means on said plunger toward said opposite end of said bore comprising third seal means engaged with said bore and adapted to wipe said bore clean of product between said opposite end thereof and said point therein when said plunger is reciprocated to project said recess into the vessel.

3. A sampling apparatus as set forth in claim 2, said bore and said plunger being cylindrical, said recess being an annular recess, and said means at said point in said bore for receiving the sample of product being a passage in said housing communicating with said bore at said point therein.

4. A sampling apparatus as set forth in claim 2, said bore and said plunger being cylindrical, and said first, second and third seal means being annular seals.

5. A sampling apparatus as set forth in claim 4, said annular seals engaging the surface of said bore and maintaining said plunger axially aligned with said bore and out of contact with the surface thereof.

6. A sampling apparatus as set forth in claim 2, said first and second seal means being on opposite sides of said point in said bore when said recess is positioned at said point and said first seal means being toward said one end of said bore, said first seal means being projected into the vessel when said recess is projected therein, said second seal means moving past said point to a position toward said one end of said bore prior to said first seal means moving out of said bore and into the vessel.

7. A sampling apparatus as in claim 6, said third seal means being in said bore adjacent said opposite end thereof when said recess is at said point in said bore, said third seal means being moved toward and adjacent to said point when said recess is projected into the vessel, said third seal means wiping said bore clean of product each time that said recess is projected into the vessel.

8. A sampling apparatus as set forth in claim 7, said bore and said cylinder rod being cylindrical, said first, second and third seal means being annular seals, said means for receiving said sample being an outlet port formed through said housing in communication with said bore at said point therein.

9. A sampling apparatus as set forth in claim 8, said housing having an inlet port formed therethrough in communication with said bore at said point therein generally opposite from said outlet port, said inlet port accommodating introduction of a flushing agent into said recess to remove the sample of product therefrom and to move the sample through said outlet port.

10. A sampling apparatus as set forth in claim 9, said bore having an enlarged chamber therein intersecting said bore at said point, said inlet and outlet ports communication with opposite sides of said chamber.

11. A sampling apparatus as set forth in claim 2, said means for reciprocating said plunger in said bore comprising a pneumatically actuated cylinder connected with said housing at said opposite end of said bore.

12. A sampling apparatus as in claim 11, including quick release clamp means connecting said pneumatically actuated cylinder with said housing at said opposite end of said bore, said clamp means being releasable to enable said plunger to be withdrawn from said bore for inspection, cleaning and replacement of parts.

13. A sampling apparatus as set forth in claim 11, said housing and said pneumatically actuated cylinder defining a space therebetween, said space being vented to atmosphere to prevent negative and positive pressures from being generated therein as said plunger is reciprocated to project and retract, respectively, said recess into and from the vessel.

* * * * *